United States Patent [19]

Rheinberger et al.

[11] Patent Number: 5,426,134
[45] Date of Patent: Jun. 20, 1995

[54] DENTAL MATERIAL

[75] Inventors: Volker Rheinberger, Vaduz, Liechtenstein; Ulrich Salz, Weissenberg, Germany; Peter Burtscher, Nütziders, Austria

[73] Assignee: Ivoclar AG, Germany

[21] Appl. No.: 81,058

[22] Filed: Jun. 25, 1993

[30] Foreign Application Priority Data

Jun. 25, 1992 [DE] Germany .............. 42 20 958.7

[51] Int. Cl.⁶ .................... C08K 5/10; C08F 2/00; C08G 73/06
[52] U.S. Cl. .................... 523/118; 526/204; 526/222; 528/424
[58] Field of Search .............. 523/115, 118, 120; 528/424; 526/204, 222; 433/201.1, 202.1

[56] References Cited

U.S. PATENT DOCUMENTS

| | | | |
|---|---|---|---|
| 3,453,242 | 7/1969 | Schmitt et al. | 260/77.5 |
| 3,538,024 | 11/1970 | Dishburger et al. | 260/2 |
| 3,634,400 | 1/1972 | Schmitt et al. | 260/239 E |
| 3,740,850 | 6/1973 | Bowen et al. | 526/204 |
| 3,872,047 | 3/1975 | Jandourek | 260/33.4 R |
| 3,878,180 | 4/1975 | Holder et al. | 526/204 |
| 4,093,555 | 6/1978 | Schmitt et al. | 252/188.3 R |
| 4,167,618 | 9/1979 | Schmitt et al. | 528/424 |
| 4,787,850 | 11/1988 | Michl et al. | 523/115 |

Primary Examiner—Paul R. Michl
Assistant Examiner—LaVonda R. DeWitt
Attorney, Agent, or Firm—Cushman, Darby & Cushman

[57] ABSTRACT

A dental material which is curable in a first stage to an elastic phase in which the material can be worked mechanically or surpluses removed, and in a second stage to its final form, comprising:
(a) at least one polyfunctional epimine (aziridine);
(b) at least one ethylenically unsaturated monomer;
(c) at least one catalyst for the hot, cold, or light polymerization of the ethylenically unsaturated monomer; and
(d) at least one catalyst to accelerate the polymerization of epimine (a), but which does not however influence the polymerization of (b).

19 Claims, 1 Drawing Sheet

DENTAL MATERIAL

BACKGROUND OF THE INVENTION

1. Field of the Invention

The present invention relates to a dental material which is curable in a first stage to an elastic phase, in which the material can be processed mechanically or surpluses can be removed, and in a second step, to its final form.

2. Background Information

Dental materials which have an elastic phase over a practice relevant processing period, which must be neither too long nor too short, are particularly well suited for special fields of use and are therefore preferred over the materials on the market at the present time.

These special fields of use are, on the one hand, the field of temporary crowns and bridges for the provisional treatment of prosthetic works and of temporary fillings for the provisional treatment, especially of several fillings situated next to one another. On the other hand, they are plastic dental cements for the cementing-in of a dental workpiece, the surpluses of which can easily be removed in this elastic phase.

The materials used for temporary crowns and bridges which are on the market, at present, are predominantly self-curing polymethacrylate/methacrylate systems, composites based on methacrylate or other polymer systems such as, for example, epimine systems.

To prepare a temporary or provisional crown or bridge, the mixed temporary crown and bridge material is placed in a suitable mould, with which the material is placed in the predetermined form on the tooth stump or stumps to be treated. The material then hardens in this impression. At a certain time, however, at which the material has still not completely hardened, the impression must be removed, together with the temporary provision. With the materials used up until now, the time period available for this is, however, very short and is often missed.

The reasons for this are that the hardening of these materials in the impression is difficult to control and that it is further influenced by many disruptive factors such as mixing conditions, temperature, moisture, etc. This has the consequence that if the crown is removed too early, the material is either still viscous or not dimensionally stable, i.e., the temporary treatment, namely, the provisional bridge or crown, must be prepared again. If, on the other hand, one waits too long, the temporary crown or bridge can no longer be removed from the stump, especially when decaying areas are present. Added to this issue is the fact that, as a rule, temperature problems are also connected with the use of these materials. The polymerization reaction which, as mentioned, is not controllable, proceeds exothermically. So much thermal energy is liberated that damage to the pulp can occur.

Similar problems occur during use as a temporary filling material. With large cavities situated next to each other (predominantly MOD), which are treated with inlays prepared in the laboratory, the provisional treatment of the cavities is frequently undertaken in such a way that the cavities situated next to each other are treated en bloc. For this purpose, the self-hardening temporary material is introduced into the isolated cavities and removed again from these cavities at a moment when the material still has a certain elasticity. If this moment is not exactly timed, problems arise as have already been described with respect to the use as temporary crown and bridge material. In most cases, hardening has proceeded too far, meaning that the temporary filling can no longer be removed. Furthermore, problems connected with temperature stress are also to be expected here.

After the temporary filling has been removed from the cavity, decaying areas are removed, and then the workpiece is fixed with a temporary cement.

A similar technique has very recently evolved for the production of chairside (i.e. at the dentist's chair) or labside (in the dental laboratory) milled ceramic inlays. As described above, the isolated cavity is filled with a so-called proinlay material and the material modelled as the final inlay fillings is to be shaped. In most cases, one also encounters problems here in removing the proinlay from the cavity, on the one hand because of the decaying areas, and on the other hand because of the need for very precise timing. The proinlay is afterwards transferred with a copying cutter into the definitive ceramic inlay. Chairside, the ceramic inlay is fitted immediately, and with the labside technique, the cavity is treated with a material described above.

It is clear from the problems described that, both for temporary crowns and bridging materials and for temporary filling materials, there is the need for a material which hardens controllably in a first stage of a certain elasticity and which remains stable over a practice-relevant period and can therefore be removed easily from the stump or from the cavity. It can then be worked and finished while still in this form and subsequently hardened in a second stage to its final form.

The other field of use mentioned above is a composite cement with possible surplus removal. When cementing-in dental workpieces such as e.g. ceramic inlays, ceramic or metal crowns with tooth-colored composite cements, it is very difficult to recognize cement surpluses and remove them as gently as possible. If the surpluses are removed in an unhardened state, the cement from the cement joint is taken out also, in most cases, resulting in a cement depletion. If, on the other hand, one tries to remove the cement surplus in the hardened state, the cement as well as the hard tooth substance are also very severely damaged in most cases.

It is clear that for this field of use, also, there is a need for a material which hardens controllably in a first stage to an elastic phase in which the workpiece is already fixed in the correct position but which allows the surpluses of the cement to be cut away with a sharp instrument such as a scalpel.

In EP-A-195 224, applicants describe a dental material for producing artificial teeth or parts such as crowns or inlays from two separate components to be mixed together during use. In a first stage, a polyfunctional isocyanate is condensed with a polyalcohol, with the help of tin catalysts, to a polyurethane which is present as an elastic phase which remains stable over an extended period of time. Then, in a second stage, at least one methacrylate compound contained in the overall system is fully cured by hot, cold, or light polymerization to artificial teeth or tooth parts.

EP-A-410 199 (Bayer) teaches plastics, fully curable in a number of steps, which consist of at least one silicopolyether, at least one radically curing monomer, at least one catalyst for hot, cold, or light polymerization, and at least one catalyst for the condensation of the silicopolyether. Such plastics based on silicopolyethers do, however, have the disadvantage that the silicopolyethers negatively influence the polymerization of the radically curing monomers. The polymerization of the second stage, i.e. of the monomers or the methacrylate, is incomplete which again has a negative effect on the physical properties of the hardened plastics. In particular, the flexural moduli of the cured plastics are unsatisfactory.

Epimines and their use in the dental field are also known. They are used particularly as molding materials and as temporary crowns and bridge materials. Epimines with a molecular weight of circa 6000 are used in molding materials, as described in DE-B-1 544 837. They polymerize to an elastic phase and in doing so serve their purpose. Short-chained epimines with a molecular weight of circa 500 are used in a temporary crown and bridge material (U.S. Pat. No. 3,453,242 and U.S. Pat. No. 4,093,555). These polymerize to a hard composition, whereby an elastic phase is passed through for a short time during the polymerization.

To the best of the knowledge of the applicants, there are no publications in the art in which a product is obtained with epimines alone, or in combination with other polymerization systems, which remains in an elastic phase over a longer period of time and then passes into a hard state after suitable activation.

SUMMARY OF THE INVENTION

It is an object of the invention to make available a dental material which is curable in a first stage to an elastic phase in which the material can be worked mechanically or surpluses can be removed, and in a second stage, to its final form. It is further the object to create a dental material which permits both the production of artificial, provisional tooth parts and the securing or cementing-in of artificial teeth and tooth parts made from ceramics or metal. The first stage guarantees an elasticity for an adequate time such that the provisional tooth parts can be prepared and the surpluses which result upon the cementing-in of the finished teeth or tooth parts can be removed without any problems. It is a particular object to make available a dental material which is suitable as a tooth replacement material for temporary crowns and bridges, as a temporary filling material, as well as proinlay material for the CAM milling technique and as composite cement for the cementing-in of a dental workpiece.

It was quite surprising and unexpected that such a material is obtained by combining an epimine and a methacrylate polymer system.

DETAILED DESCRIPTION OF THE INVENTION

Figure 1:
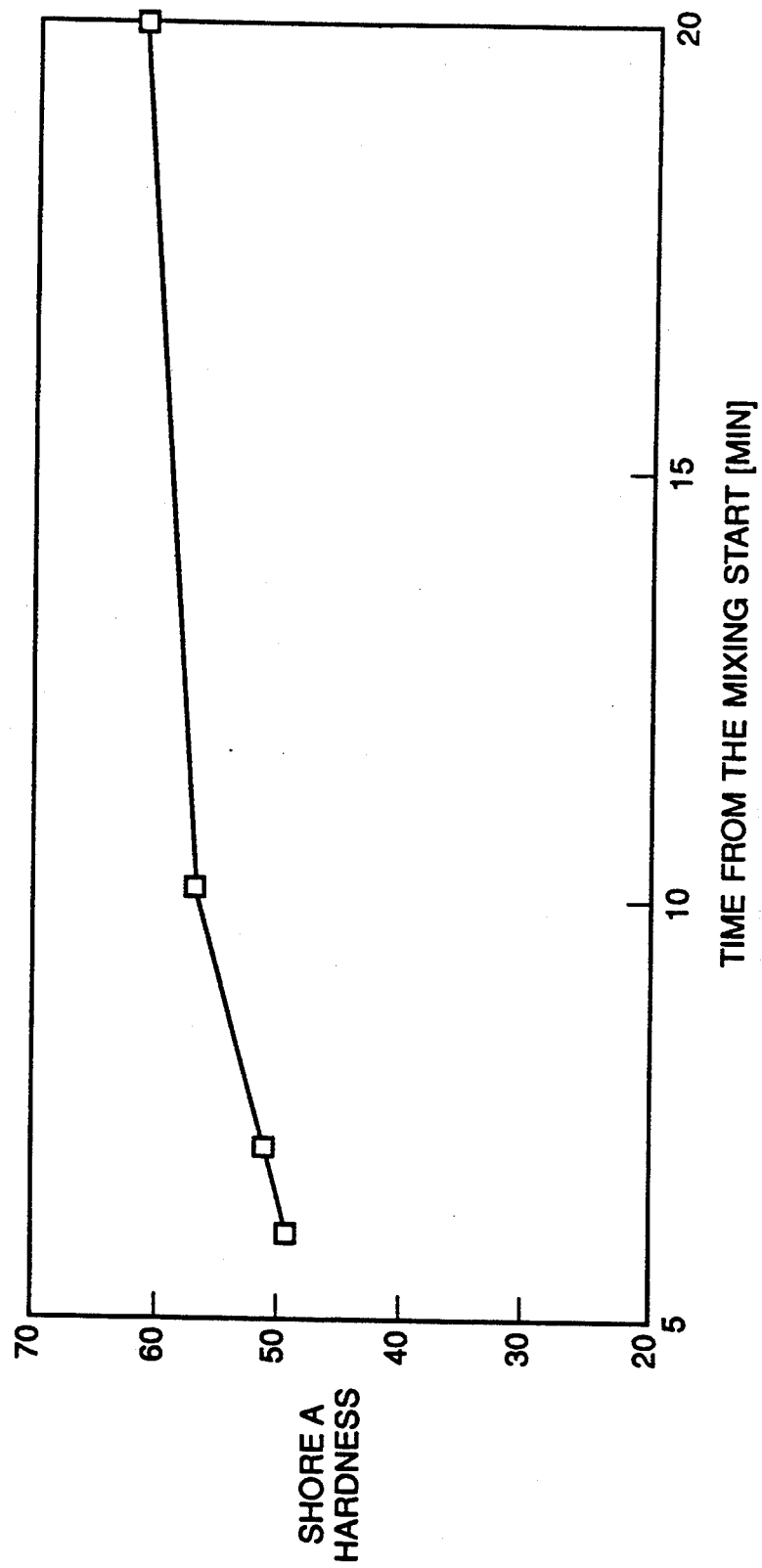
FIG. 1 represents the hardness pattern of the elastic phase.

To achieve the object of the invention, a dental material is therefore proposed which is curable in a first stage to an elastic phase in which the material can be worked mechanically or surpluses removed, and in a second stage, to its final form. The dental material comprises:

(a) at least one polyfunctional epimine (aziridine),
(b) at least one ethylenically unsaturated monomer,
(c) at least one catalyst for the hot, cold, or light polymerization of the ethylenically unsaturated monomer and
(d) at least one catalyst to accelerate the polymerization of epimine (a) which does not, however, influence the polymerization of (b).

The material is preferably present in two separate components: a first component or base component and a second component or base activator component, which are mixed together during use, preferably in a ratio of 1:1.

It is also preferred that the material comprises an inorganic filler, organic filler, or a mixture thereof.

Unlike the aforementioned known interstitial or interspace polymers with which the first stage, i.e. the stage of the elastic phase, is obtained by polycondensation or condensation polymerization of a polyfunctional isocyanate with a polyalcohol, according to the invention, the elastic phase is achieved according to an entirely different polymerization mechanism, namely by cationic polymerization. In this cationic polymerization, polyfunctional imines (synonymous with aziridine or ethylenimine compounds) are polymerized to an elastic phase.

The epimines used in the dental material of the invention for the polymerization to the elastic phase are produced according to the process described in DE-B-1 544 837. The cross-linkers or catalysts used for the cationic polymerization are usual cationizing activators or starters, preferably arylsulphonic acid esters according to DE-B-1 544 837, particularly, 2,5-dichlorobenzene sulphonic acid methyl esters and special sulphonium salts according to U.S. Pat. No. 4,167,618, corresponding to DE-A-2 515 593.

The elastic phase achieved with this cationic polymerization remains stable over a practice-relevant period of ca. 3 to 30 minutes. This is represented in FIG. 1 by the hardness pattern of the elastic phase in relation to the time from the start of mixing. The polymerization of the first stage until the elastic phase is reached takes place at a temperature of 20° to 37° C.

The dental material of the invention must further contain at least one ethylenically unsaturated monomer. Suitable ethylenically unsaturated monomers of this type are methacrylate and acrylates, preferably mono- or polyfunctional methacrylate, particularly isobutylmethacrylate, tetraethylene glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decandiol dimethacrylate, dodecandiol dimethacrylate, bisphenol-A-dimethacrylate, trimethylol propane trimethacrylate, 2,2-bis-4(3-methacryloxy-2-hydroxy)-phenylpropane(bis-GMA) and reaction produces of di- and/or triisocyanates and OH-group-containing methacrylate.

Suitable catalysts for the hot polymerization of the ethylenically unsaturated monomer are the usual ones, for example, peroxides such as dibenzoyl peroxide, dilauroyl peroxide, tert.-butylperoctoate, tert.-butylperbenzoate, but also α,α'-azo-bis-(isobutyroethylester), AIBN, benzpinacol and 2,2'-dimethylbenzpinacol.

Suitable catalysts for the cold polymerization of the ethylenically unsaturated polymers are the usual ones, particularly amine/peroxide systems (e.g., dibenzoyl peroxide/N,N-dimethyl-p-toluidine).

Suitable as catalysts for the light polymerization of the ethylenically unsaturated polymers are benzophenone and its derivatives, benzoin and its derivatives, acetyl phosphinic oxides, especially α-diketones such as camphor quinone, optionally combined with an amine as a reducing agent.

The dental material preferably contains at least one inorganic and/or organic filler. Suitable for this purpose are, for example, AEROSIL® (fumed $SiO_2$), barium silicate glass which is preferably silanized, precipitated silicic acid, oxides or mixed oxides obtained by the sol-gel process, X-ray-opaque lanthanide compounds such as e.g. $YbF_3$, strontium, barium and Li—Al silicate glasses, whereby the oxidic compounds are preferably silanized. Stabilizers, dyestuffs or other auxiliaries can also be present.

Likewise, prepolymers which are obtained from one or more of the aforementioned fillers as well as one or more ethylenically unsaturated monomers obtained by hot curing and subsequent grinding are suitable.

Production of the dental material of the invention is effected by simply mixing the components, preferably in a ratio of 1:1, whereby the aziridine (a) is incorporated only in the first component and the cationizing starter (d) only in the second component. The ethylenically unsaturated monomer is present preferably in both the first and the second component. The catalyst (c) activating the polymerization of the ethylenically unsaturated polymer is preferably used in the first component with the light- and hot polymerizations, and the amine/-peroxide catalyst system (c) employed for the cold polymerization is used separately in both components.

The polyfunctional epimine (a) is preferably used in a quantity of 5 to 70 wt. %, especially preferably 6 to 40 wt. %, relative to the first component, the base component. Relative to the whole mixture, i.e. the components mixed together, (a) is used preferably in an amount of 2.0 to 35 wt. %, especially preferably 2.5 to 20 wt. %.

The ethylenically unsaturated monomer (b) is preferably used in both mixtures in a range from 10 to 80 wt. %, preferably 15 to 50 wt. % of the total mixture.

The catalysts (c) are preferably incorporated in an amount of 0.01 to 5 wt. %, relative to the total material.

The cationizing starter (d) is preferably used in a quantity of 0.1 to 5 wt. %, relative to the second component, relative to the total material in a quantity of 0.05 to 2.5 wt. %.

The filler is preferably used in quantities of 20 to 80 wt. %, relative to the total material.

In the following examples, two different epimines, produced according to DE-B-1 544 837, were used. In one case, polytetrahydrofuran with an average molecular weight of 1200 was used as the diol component (subsequently called PTHF epimine), and in the other case polyethylene glycol with an average molecular weight of 6000 was used as the diol component (subsequently called PE epimine).

EXAMPLE 1

Temporary Crown and Bridge Material

Base Activator Paste 1.5 wt. % 2,5-dichlorobenzene sulphonic acid methyl ester and 0.1 wt. % 3,5-di-t-butyl-4-hydroxytoluene were dissolved in 8.8 wt. % triethyleneglycol dimethacrylate and 17.5 wt. % UDMA*. 66.0 wt. % Ba silicate glass (silanized) and 6.1 wt. % AEROSIL® Ox-50 (silanized) were then added in a kneader.
*Reaction product of 1 mol 2,2,4-trimethylhexamethylene diisocyanate with 2 mol hydroxyethyl methacrylate (HEMA)
Base Paste:

0.08 wt. % camphor quinone and 0.16 wt. % N-2-cyanoethyl-N-methyl-aniline were dissolved in 4.6 wt. % triethylene glycol dimethylacrylate and 9.16 wt % UDMA*. 5.6 wt. % PTHF epimine, 8.4 wt. % PE epimine and 72.0 wt. % Ba silicate glass (silanized) were added in a kneader.
*Reaction product of 1 mol 2,2,4-trimethylhexamethylene diisocyanate with 2 mol hydroxyethyl methacrylate (HEMA)

An easily miscible two-component dental material was obtained in this manner. After mixing in a ratio of 1:1, the material hardens at a temperature of 37° C. after 2.1 minutes to an elastic phase.

Measurement of the hardness in relation to time yielded:

| Time from start of mixing (min) | Shore A Hardness |
| --- | --- |
| 6 | 49 |
| 7 | 51 |
| 10 | 57 |
| 20 | 62 |

These figures show that the elastic phase is stable over a period of at least approximately 20 minutes (FIG. 1).

The material was then converted into its final form by irradiation with a halogen light apparatus (Heliomat®) for 40 seconds. The material obtained had the following properties:

Flexural strength: 39 MPa
Flexural modulus: 3200 MPa

EXAMPLE 2

Securing Composite with Possible Surplus Removal

Base Activating Paste 1.8 wt. %, 2,5-dichlorobenzene sulphonic acid methyl ester, 0.8 wt. % benzoyl peroxide (50%) and 0.06 wt. % 3,5-di-t-butylhydroxy toluene were dissolved in 14.2 wt. % triethylene glycol dimethylacrylate and 14.14 wt. % ethoxylated bis-glycidyl-methacrylate (bis-GMA). 69.0 wt. % Ba silicate glass (silanized) were then added in a kneader.
Base Paste 0.07 wt. % camphor quinone, 0.07 wt. % N-cyanoethyl-N-methyl-aniline, 0.03 wt. %, 3,5-di-t-butyl-4-hydroxytoluene and 0.1 wt. % N,N-diethanol-3,5-di-t-butyl aniline were dissolved in 11.6 wt. % triethylene glycolmethacrylate and 11.6 wt. % ethoxylated bis-GMA. 3.5 wt. % PTHF epimine, 3.5 wt. % PE epimine and 69.53 wt. % Ba silicate glass (silanized) were then added in a kneader.

An easily miscible two-component composite cement was obtained in this manner. After mixing in a ratio of 1:1, the material hardened at a temperature of 37° C. after 3 minutes to an elastic phase. After two minutes more, self-hardening of the amine/peroxide system started.

What is claimed is:

1. A dental material comprising:
   (a) at least one polyfunctional epimine;
   (b) at least one ethylenically unsaturated monomer;
   (c) at least one catalyst for the hot, cold, or light polymerization of the ethylenically unsaturated monomer; and
   (d) at least one catalyst to accelerate the polymerization of the epimine (a) which does not influence the polymerization of (b), wherein said dental material is present in two separate components, a base component and a base activator component, said components being mixed together during use, and wherein said material is curable in a first stage to an elastic phase in which said dental material can be worked mechanically or in which cement surpluses can be removed, and is curable in a second stage to a final form.

2. The dental material according to claim 1, wherein said components are mixed together during use in a ratio of 1:1.

3. The dental material according to claim 2, wherein (a) is present only in the base component; (b) and (c) are present in the base component and optionally (b) and (c) are also present in the base activator, and (d) is present only in the base activator component.

4. The dental material according to claim 1, wherein said dental material further contains at least one inorganic filler, organic filler, or a mixture thereof.

5. The dental material according to claim 1, wherein said elastic phase remains stable for a period of at least approximately 3 to 30 minutes.

6. The dental material according to claim 1, wherein said ethylenically unsaturated monomer is a methacrylate or acrylate.

7. The dental material according to claim 1, wherein said dental material comprises an α-diketone, optionally combined with an amine as reducing agent, as catalyst (c) for the light polymerization of the ethylenically unsaturated monomer.

8. The dental material according to claim 1, wherein said dental material comprises systems of amine and peroxide as catalyst (c) for the cold polymerization of the ethylenically unsaturated monomer.

9. The dental material according to claim 1, wherein said dental material comprises, as catalyst (d), an aryl sulphonic acid ester.

10. The dental material according to claim 9, wherein said aryl sulfonic acid ester is an electronegatively substituted aryl sulfonic methyl ester.

11. The dental material according to claim 1, wherein said dental material comprises:
(a) in a quantity of 2.0 to 35 wt. %;
(b) in a quantity of 10 to 80 wt. %;
(c) in a quantity of 0.01 to 5 wt. %; and
(d) in a quantity of 0.05 to 2.5 wt. %.

12. The dental material according to claim 11, wherein (a) is present in a quantity of 2.5 to 20 wt. % and (b) is present in a quantity of 15 to 50 wt. %.

13. The dental material according to claim 3, wherein said dental material comprises (a) in a quantity of 5 to 70 wt. %, relative to the first component; and (b) in a quantity of 0.01 to 5 wt. %, relative to the second component.

14. The dental material according to claim 13, wherein (a) is present in a quantity of 6 to 40 wt. %.

15. The dental material according to claim 3, wherein (b) is also in the base activator component.

16. A dental material comprising:
(a) at least one polyfunctional epimine;
(b) at least one ethylenically unsaturated monomer;
(c) at least one catalyst for the hot, cold, or light polymerization of the ethylenically unsaturated monomer; and
(d) at least one catalyst to accelerate the polymerization of the epimine (a) which does not influence the polymerization of (b) comprising a sulphonium salt corresponding to the general formula

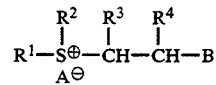

wherein $R^1$ is an alkyl group having 1 to 18 C-atoms; $R^2$ is an alkyl group having 1 to 18 C-atoms or a phenyl alkyl group having 7 to 18 C-atoms, and $R^3$ and $R^4$ are selected from a hydrogen atom, an alkyl group having 1 to 18 C-atoms, and an aryl group, wherein said alkyl groups $R^3$ and $R^4$, or $R^3$ or $R^4$ can form together with B, a cycloaliphatic or a heterocyclic ring; and B is an electron-attracting radical selected from the group consisting of carbonyl, sulfonyl, nitrile, carbon ester, chlorophenyl, nitrophenyl, benzoyl and substituted carbonyl amide; and A is a non-nucleophilic anion, wherein said dental material is present in two separate components, a base component and a base activator component, said components being mixed together during use, and wherein said material is curable in a first stage to an elastic phase in which said dental material can be worked mechanically or surpluses removed, and is curable in a second stage to a final form.

17. The dental material according to claim 16, wherein $R^2$ may contain an ester group, an ether group, or both groups.

18. The dental material according to claim 16, wherein said aryl group is substituted by a chloro-, nitro- or alkoxy- group.

19. A dental material comprising:
(a) at least one polyfunctional epimine comprising an ethylenimine compound, in which, on the average, more than one ethylenimine group has been introduced at the ends or at side chains of essentially linear polyesters, polythioethers or saturated polyesters having a mean mole weight of 1000 to 25000, said ethylenimine group having the general formula

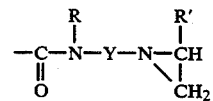

wherein R and R' are a hydrogen atom or an alkyl group and Y is a bivalent, organic group;
(b) at least one ethylenically unsaturated monomer;
(c) at least one catalyst for the hot, cold, or light polymerization of the ethylenically unsaturated monomer; and
(d) at least one catalyst to accelerate the polymerization of the epimine (a) which does not influence the polymerization of (b), wherein said dental material is present in two separate components, a base component and a base activator component, said components being mixed together during use, and wherein said material is curable in a first stage to an elastic phase in which said dental material can be worked mechanically or in which cement surpluses can be removed, and is curable in a second stage to a final form.

* * * * *